United States Patent
Shimono et al.

(10) Patent No.: US 7,604,820 B1
(45) Date of Patent: Oct. 20, 2009

(54) SOLID PREPARATION CONTAINING CHITOSAN POWDER AND PROCESS FOR PRODUCING THE SAME

(75) Inventors: Norihito Shimono, Kobe (JP); Masaaki Mori, Otsu (JP); Yutaka Higashi, Osaka (JP)

(73) Assignee: Dainippon Sumitomo Pharma Co., Ltd., Osaka (JP)

(*) Notice: Subject to any disclaimer, the term of this patent is extended or adjusted under 35 U.S.C. 154(b) by 9 days.

(21) Appl. No.: 10/048,063

(22) PCT Filed: Aug. 7, 2000

(86) PCT No.: PCT/JP00/05279

§ 371 (c)(1),
(2), (4) Date: Jan. 28, 2002

(87) PCT Pub. No.: WO01/10467

PCT Pub. Date: Feb. 15, 2001

(30) Foreign Application Priority Data

Aug. 9, 1999 (JP) .............................. 1999/224777

(51) Int. Cl.
*A61K 9/22* (2006.01)
*A61K 9/50* (2006.01)

(52) U.S. Cl. ...................... 424/468; 424/490; 424/494; 424/495; 424/497

(58) Field of Classification Search .................. 424/480, 424/466, 451, 502, 501, 464, 489–495, 488, 424/487, 468, 486
See application file for complete search history.

(56) References Cited

U.S. PATENT DOCUMENTS

| | | | | |
|---|---|---|---|---|
| 5,188,840 A | * | 2/1993 | Iida et al. ................... | 424/468 |
| 5,217,720 A | * | 6/1993 | Sekigawa et al. ........... | 424/480 |
| 5,283,064 A | * | 2/1994 | Suzuki et al. ............... | 424/451 |
| 5,731,006 A | * | 3/1998 | Akiyama et al. ............ | 424/502 |
| 5,744,166 A | * | 4/1998 | Illum .......................... | 424/501 |
| 5,840,332 A | * | 11/1998 | Lerner et al. ................ | 424/464 |
| 6,197,322 B1 | * | 3/2001 | Dutkiewicz et al. ......... | 424/412 |
| 6,368,629 B1 | | 4/2002 | Watanabe et al. | |
| 6,506,407 B2 | | 1/2003 | Watanabe et al. | |

FOREIGN PATENT DOCUMENTS

| | | |
|---|---|---|
| CA | 2305762 | 4/1999 |
| EP | 466566 | 1/1992 |
| GB | 2 255 344 A | 11/1992 |
| GB | 2255344 | 11/1992 |
| JP | 4-247026 | 9/1992 |
| JP | 04-247026 | 9/1992 |
| JP | 4-264021 | 9/1992 |
| JP | 04-264021 | 9/1992 |
| JP | 04-264022 | 9/1992 |
| JP | 4-264022 | 9/1992 |
| JP | 04-264023 | 9/1992 |
| JP | 4-264023 | 9/1992 |
| JP | 07-002701 | 1/1995 |
| JP | 7-2701 | 1/1995 |
| KR | 1997-7002071 | 5/1997 |
| WO | 89/00045 | 1/1989 |
| WO | 95/28963 | 11/1995 |
| WO | 99/18938 | 4/1999 |

* cited by examiner

Primary Examiner—Michael G Hartley
Assistant Examiner—Micah-Paul Young
(74) Attorney, Agent, or Firm—Wenderoth, Lind & Ponack, L.L.P.

(57) ABSTRACT

A colonic delivery solid preparation containing chitosan powder, which can control the dissolution of a medicament therefrom in the large intestine and release the medicament contained therein specifically in the large intestine, obtained by successively coating a medicament-containing solid material with (1) a water-insoluble polymer having a chitosan powder dispersed therein and (2) an enteric polymer; and a solid preparation containing chitosan powder, which can partly release a medicament in the stomach and, after passing through the small intestine, disintegrate at an accelerated rate in the large intestine and release a medicament in the large intestine, obtained by coating a medicament-containing solid material with a water-insoluble polymer having a chitosan powder dispersed therein.

6 Claims, 11 Drawing Sheets

A.

B.

SOLID PREPARATION CONTAINING CHITOSAN POWDER AND PROCESS FOR PRODUCING THE SAME

This application is a 371 of PCT/JP00/05279 filed Aug. 7, 2000.

TECHNICAL FIELD

The present invention relates to a colonic delivery solid preparation, more particularly a colonic delivery solid preparation containing chitosan powder designed to pass through the stomach or the small intestine without disintegration, but to disintegrate in the large intestine and release a medicament therefrom when administered orally, and further relates to a sustained release solid preparation containing chitosan powder designed to partly disintegrate in the stomach and release a part of the medicament therefrom, to release the medicament in the small intestine without disintegration, and after passing through the small intestine, to disintegrate at an accelerated rate in the large intestine whereby the remaining medicament in the preparation is released in the large intestine.

BACKGROUND ART

Chitosan is a natural polymer which is obtained by N-deacetylating a polysaccharide chitin in a conc. alkaline solution, said chitin being present in abundance in the exoskeleton of crustaceans or insects, and chitosan per se has been used as a colonic delivery substance because it disintegrates specifically by *Escherichia coli*. Several pharmaceutical compositions containing chitosan, which can release the medicament therefrom specifically in the large intestine, have been known hitherto.

For instance, JP-A-4-69333 discloses a colonic delivery solid preparation, which is obtained by successively coating a solid medicament with a chitosan layer and an enteric coating layer containing as a main material hydroxypropyl methylcellulose acetate succinate or hydroxypropyl methylcellulose hexahydrophthalate.

JP-A-7-2701 discloses a pharmaceutical composition comprising a micronized cellulose and a water-soluble chitosan having a deacetylation degree of 40-60 mole % in a ratio of 20 to 200% by weight to the amount of the micronized cellulose, which can pass through the small intestine and disintegrate in the large intestine, and a process for producing the same.

Since chitosan is usually soluble only in an acidic aqueous solution but hardly soluble in an organic solvent, it is necessary to dissolve chitosan in an acidic aqueous solution in order to use it for coating a naked solid preparation in the process of preparing a colonic delivery solid preparation. However, it is very difficult to completely remove the acid contained in the acidic aqueous solution of chitosan after the coating step, and it cannot be helped for the acid to remain in the chitosan coating film, which causes some problems such as reduction of water resistant of the chitosan coating film and the harmful effects of the acid on the medicament per se. In order to overcome these defects, the above-mentioned JP-A-4-69333 suggests forming in advance an enteric coating film inside of the chitosan layer, but this method needs an extra coating step and hence it is not desirable.

In addition, in the above-mentioned JP-7-2701, various harmful results due to the acid used in the dissolution of chitosan are avoided by using a water-soluble chitosan having a deacetylation degree of 40-60%. However, when such a water-soluble chitosan is used, it is difficult to control the release of the medicament in the large intestine, while the solid preparation of the present invention can make it possible as mentioned below.

DISCLOSURE OF INVENTION

The present inventors have intensively studied on a colonic delivery solid preparation being capable of controlling the release of a medicament by a simpler method, and have found a solid preparation containing chitosan powder, which can release the medicament specifically in the large intestine and control the release of the medicament in the large intestine, which is obtained by coating successively a medicament-containing solid material with (1) a water-insoluble polymer having a chitosan powder dispersed therein, and (2) an enteric polymer. Moreover, they have also found a sustained release solid preparation containing a chitosan powder, which can partly disintegrate in the stomach and release a part of the medicament, and after passing through the small intestine, disintegrate at an accelerated rate in the large intestine, whereby the remaining medicament is released, which is obtained by coating a medicament-containing solid material only with a water-insoluble polymer having a chitosan powder dispersed therein.

The present invention provides a colonic delivery solid preparation containing a chitosan powder, which is obtained by coating successively a medicament-containing solid material with (1) a water-insoluble polymer having a chitosan powder dispersed therein, and (2) an enteric polymer; a process for producing a colonic delivery solid preparation containing chitosan powder, which comprises coating a medicament-containing solid material with a water-insoluble coating polymer having a chitosan powder dispersed therein, and further coating the resultant with an enteric polymer; and further provides a sustained release solid preparation for producing the above-mentioned colonic delivery solid preparation containing chitosan powder, more particularly, a sustained release solid preparation containing chitosan powder which is obtained by coating a medicament-containing solid material with a water-insoluble polymer having a chitosan powder dispersed therein; and a process for producing the same.

BEST MODE FOR CARRYING OUT THE INVENTION

Figure 1:
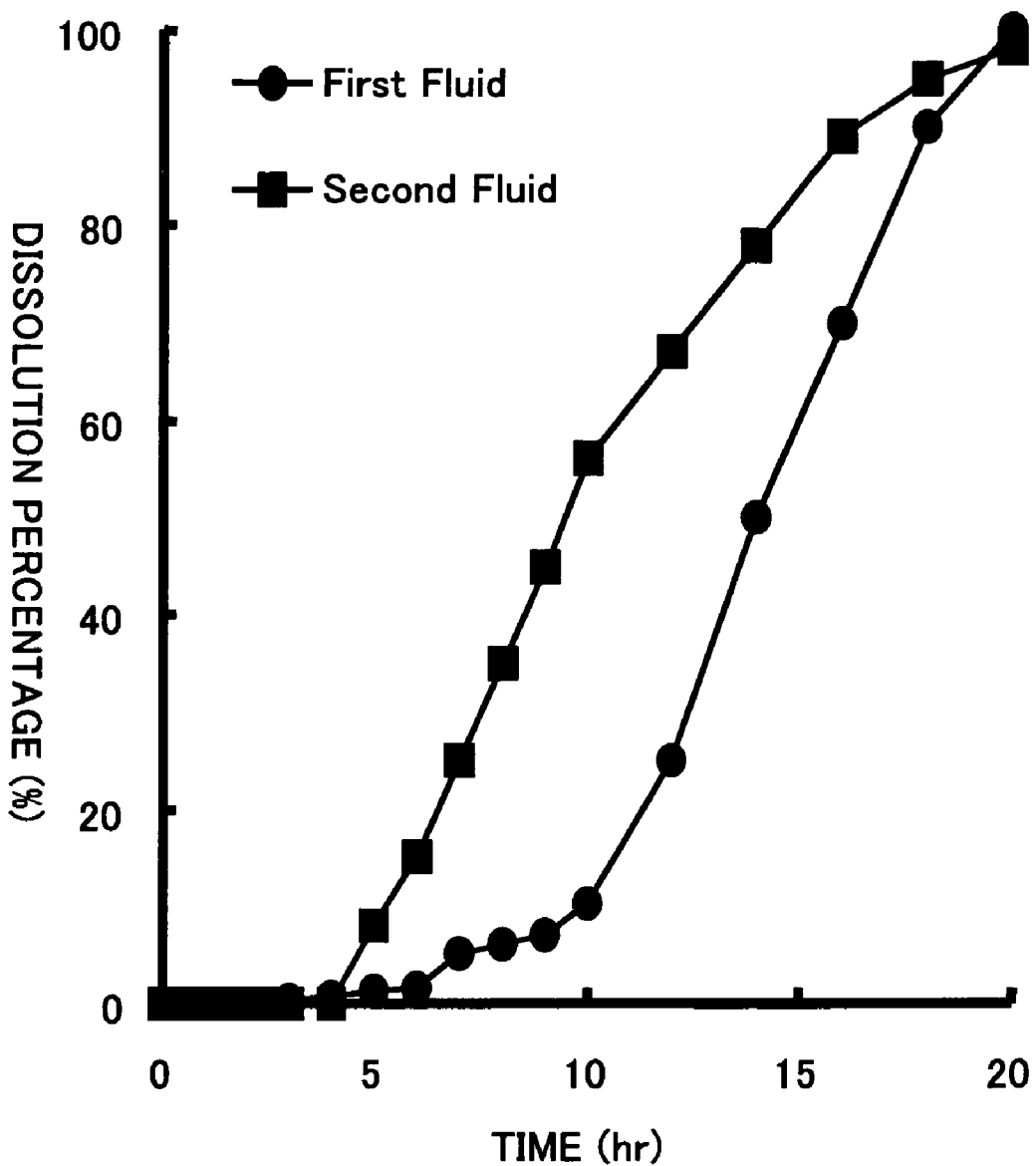
FIG. 1 shows the relation between the dissolution percentage of the medicament and the time of the colonic delivery pellet preparation of Example 1 in the dissolution test by Paddle method using Japanese Pharmacopoeia 1st Fluid and Japanese Pharmacopoeia 2nd Fluid.

The "medicament-containing solid material" means a medicament or a mixture of a medicament and a pharmaceutical excipient, and may be in the form of a powder, a granule, a pellet, a capsule, or a tablet, which can be coated, and it is preferably in the form of a pellet, a capsule or a tablet.

The pharmaceutical excipient may include conventional components for a pharmaceutical preparation such as a filler, a binder, a disintegrant, a lubricant, a glidant, etc., which are usually used in the pharmaceutical field.

Chitosan used in the present invention is obtained by deacetylation of chitin, is a straight chain polysaccharide bonded to an N-acetyl-D-glucosamine via a β(1-4) bond, and being present in the shells of crabs or shrimps, the outer skin of insects, the organs of mollusc such as cuttlefish and shellfish, or in the cell wall of fungi (e.g., mushroom), and it is usually one being deacetylated to the extent of about 60% or more, for example, to the extent of about 60% to about 100%. All of commercially available chitosan for food or for medical use can be used in the present preparation but the preferable chitosan is one being deacetylated to the extent of about 75% to about 98%.

The water-insoluble polymer forming a water-insoluble coating film (hereinafter, occasionally referred to as "water-insoluble substance") may be any one which is usually used in this field (cf., Directory of Pharmaceutical Excipients (in Japanese), published on Nov. 25, 1992, by Yakuji Jiho Co., Ltd.; Aqueous Polymeric Coatings for Pharmaceutical Dosage Forms, Drugs and the Pharmaceutical Sciences, vol. 36, p. 161-167 (1989)), for example, water-insoluble acrylate copolymers such as ethyl acrylate-methyl methacrylate-trimethylammoniumethyl methacrylate chloride copolymer (=poly(ethyl acrylate, methyl methacrylate, trimethyl-ammonioethyl methacrylate chloride), Eudragit® RS or Eudragit® RL (Röhm and Pharma, Co., Ltd.)), methyl methacrylate-ethyl acrylate copolymer (=poly(ethyl acrylate, methyl methacylate), Eudragit® NE30D (Röhm and Pharma, Co., Ltd.)), etc.; water-insoluble cellulose derivatives such as ethyl cellulose (e.g., Ethocel® (Shin-Etsu Chemical Co., Ltd.)), methyl cellulose (e.g., Methocel® (Shin-Etsu Chemical Co., Ltd.)), cellulose acetate, etc.; water-insoluble vinyl derivatives such as polyvinyl acetate, polyvinyl chloride, etc.; or a combination of two or more of these polymers. Among them, ethyl cellulose, ethyl acrylate-methyl methacrylate-trimethylammoniumethyl methacrylate chloride copolymer (Eudragit® RS), methyl methacrylate-ethyl acrylate copolymer (Eudragit® NE30D) are more preferable.

These water-insoluble polymers are dissolved in a solvent, and thereto is dispersed a chitosan powder to give a coating solution for water-insoluble coating film.

In addition, the above coating solution for water-insoluble coating film may additionally contain conventional components usually used as lubricant, glidant or aggregation inhibitor, for example, talc, magnesium stearate, light anhydrous silicic acid, glyceryl monostearate, etc.

The solvent for dissolving the water-insoluble polymer should be selected according to the properties of the water-insoluble substance to be dissolved, and includes, for example, ethanol, dichloromethane, a mixture of ethanol and dichloromethane, etc., and among them, ethanol is preferable.

In addition to the above coating solution, an aqueous coating solution may also be usable, for example, an aqueous dispersion type coating solution prepared by dispersing chitosan in an aqueous dispersion of ethyl cellulose (e.g., Aquacoat® (FMC Corporation)), methyl methacrylate-ethyl acrylate copolymer (e.g., Eudragit® NE30D (Röhm and Pharma, Co., Ltd.)), or ethyl acrylate-methyl methacrylate-trimethylammoniumethyl methacrylate chloride copolymer (e.g., Eudragit® RS30D, Eudragit® RL30D (Röhm and Pharma, Co., Ltd.)).

The thickness of the above water-insoluble coating film is not necessarily specified, and may vary according to dosage forms, the types and the content of the medicament to be contained therein, and further the amount of chitosan to be contained, etc., and it is usually in the range of about 0.05 μm to about 5 mm, preferably in the range of about 0.1 μm to about 3 mm, more preferably in the range of about 0.2 μm to about 2 mm.

When a colonic delivery solid preparation is prepared, the compounding ratio of the chitosan powder to the water-insoluble polymer may be in any possible range, but preferably in the range of about 1:20 to about 20:1 (by weight, hereinafter the same), more preferably in the range of about 1:10 to about 10:1, and especially preferably in the range of about 1:4 to about 4:1.

When a sustained release solid preparation is prepared, the compounding ratio of the chitosan powder to the water-insoluble polymer may be in any possible range, but preferably in the range of about 1:20 to about 20:1, more preferably in the range of about 1:10 to about 10:1, and especially preferably in the range of about 1:4 to about 4:1.

The particle diameter of the chitosan powder used in both cases is usually not greater than 700 μm, for example, in the range of about 700 μm to 0.05 μm, preferably in the range of about 500 µm to about 0.1 µm, and more preferably in the range of about 300 µm to about 0.1 µm. The mean particle diameter is in the range of about 0.5 µm to about 400 µm, preferably in the range of about 1 µm to about 200 µm. In addition, the particle diameter of the chitosan powder is occasionally expressed by a particle size passing through a sieve, for example, it is preferable to use the chitosan powder passing through a sieve of 60 mesh (250 µm) to 80 mesh (177 µm).

The enteric polymer forming an enteric coating film (hereinafter, occasionally referred to as "enteric substance") may be any conventional ones which are usually used in this field, and includes, for example, one or more selected from the group consisting of carboxymethylethyl cellulose (CMEC), hydroxypropyl methylcellulose acetate succinate (HPMCAS (Shin-Etsu Chemical Co., Ltd.)), hydroxypropyl methyl-cellulose phthalate (HPMCP (Shin-Etsu Chemical Co., Ltd.)), cellulose acetate phthalate, shellac, acrylate copolymers (e.g., methacrylic acid-ethyl acrylate copolymer such as Eudragit® L100-55, methacrylic acid-methyl methacrylate copolymer such as Eudragit® L100, S100). The preferable enteric substance includes, for example, hydroxypropyl methylcellulose acetate succinate (HPMCAS), hydroxypropyl methylcellulose phthalate (HPMCP) and methacrylic acid ethyl acrylate (Eudragit® L100-55). These enteric substances are dissolved in the same solvent as those for the above-mentioned coating solution for water-insoluble coating film to give a coating solution for enteric coating film.

Further, the above coating solution for enteric coating film may additionally contain other components used as lubricant, glidant or aggregation inhibitor such as talc, magnesium stearate, light anhydrous silicic acid, glycerin monostearate, etc.

The thickness of the above enteric coating film is not necessarily specified and may vary according to dosage forms, the types and content of the medicament contained therein, and the amount of chitosan, etc., but it is usually in the range of about 0.05 µm to about 5 mm, preferably in the range of about 0.1 µm to about 3 mm, and more preferably in the range of about 0.2 µm to about 2 mm.

The medicament used in the present invention may be ones being water-soluble or water-hardly-soluble, or one having any other solubility, and the types thereof are not necessarily specified, and includes, for example, 5-aminosalicylic acid (5-ASA) being effective to irritable bowel syndrome, or protein preparations or insulin preparations.

The colonic delivery solid preparation containing chitosan powder of the present invention will be explained in more detail below.

Figure 11:
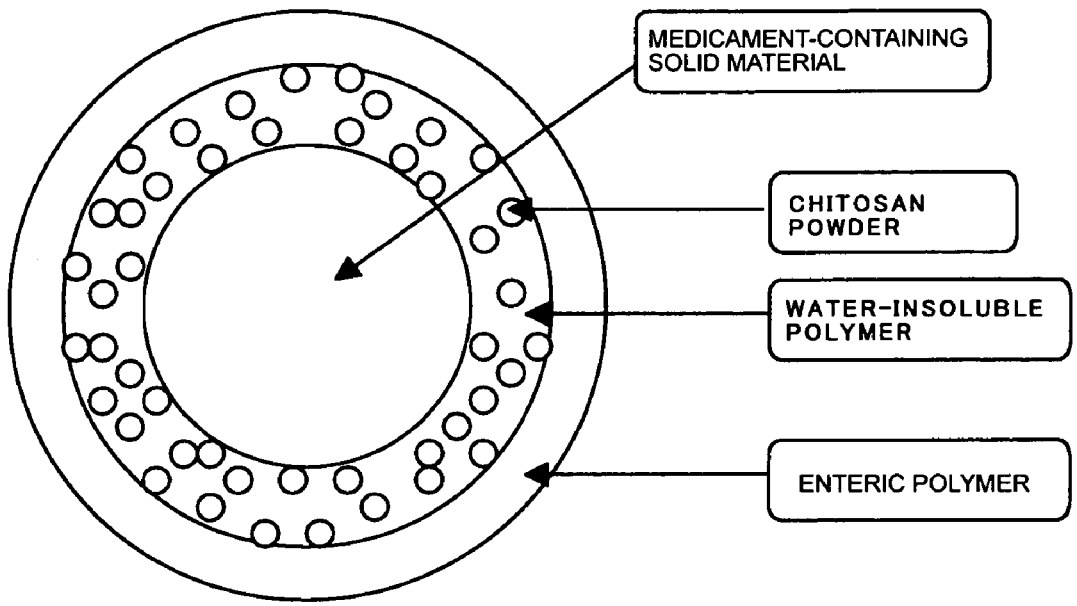
FIG. 11A shows a fundamental structure of the colonic delivery solid preparation containing chitosan powder.
FIG. 11B shows a fundamental structure of the sustained release solid preparation containing chitosan powder.
Figure 11:
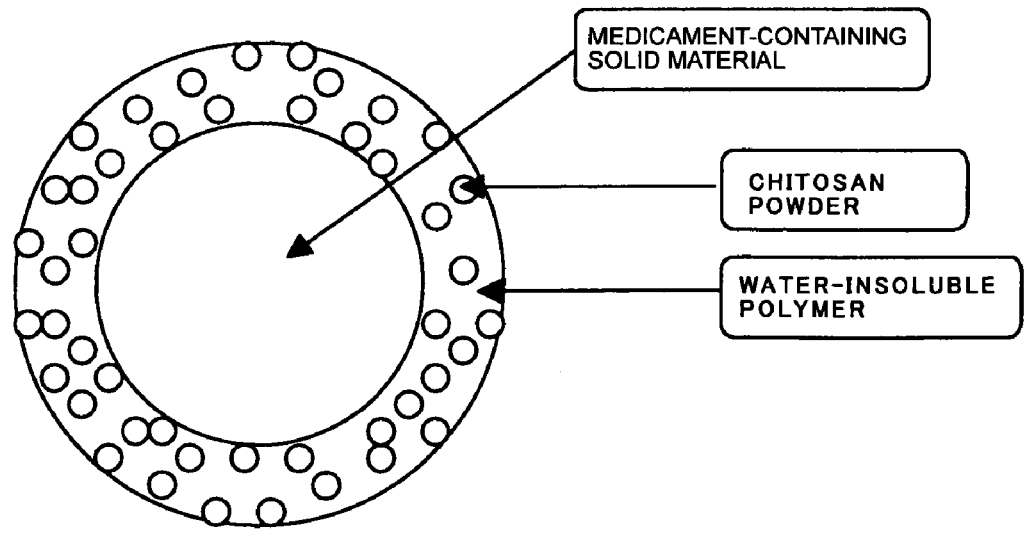

As is illustratively shown in FIG. 11A, the colonic delivery solid preparation of the present invention has a medicament-containing solid material at the center thereof, and can be prepared by forming a water-insoluble coating film consisting of chitosan and a water-insoluble polymer around the core, and then further forming an enteric coating film made of an enteric polymer around said water-insoluble coating film. To be more precise, a coating solution for water-insoluble coating film obtained by dispersing a chitosan powder in various water-insoluble polymer solution is coated, for example, onto a medicament-containing solid material such as capsules, tablets or pellets, and further a coating solution for enteric coating film is applied thereon at the most outer layer to form an enteric coating film. The solvent used in each coating solution is removed after the coating procedure by natural drying of the resulting solid preparation, or by drying under heating in an apparatus at a temperature of the range from about 30° C. to about 80° C., preferably at a temperature of the range from about 40° C. to about 60° C.

The preferable dosage form is a solid preparation containing chitosan powder, which is obtained by forming a coating film with a dispersion of a chitosan powder in various water-insoluble polymers around capsules or tablets in which a medicament or a mixture of a medicament and a pharmaceutical excipient is filled, and further by coating around the resultant with an enteric coating solution.

More preferable dosage form is a solid preparation containing chitosan powder, which is obtained by charging a commercially available particulate material such as particulate crystalline cellulose (e.g., Celphere® (Asahi Kasei Corporation)), purified sucrose spheres, white sugar starch spheres (e.g., various Nonpareil®, Freund Industrial Co., Ltd.) into a coating apparatus, coating the core particulate material with a medicament or a mixture of a medicament and a pharmaceutical excipient to give a medicament-containing solid material, coating around said solid with a coating film containing a chitosan powder dispersed in various water-insoluble polymers, and further coating the outer thereof with an enteric coating film.

The colonic delivery solid preparation of the present invention has the following pharmaceutical characteristics.

The Medicament is not Released in the Stomach, and the Release Thereof in the Large Intestine is Controlled.

The present solid preparation possesses such a property that the medicament therein is not released during the preparation passes through the stomach, because of the enteric coating film on the most outer layer thereof, and said enteric coating film can be first dissolved in the small intestine. In case of a human, the small intestine transit time is constant in the range of 3±1 hours, and in order to achieve the release of the medicament in the large intestine, it is considered that the lag time for colonic delivery is preferably in the range of which a little time is added to the above transit time, i.e., in the range of about 2 hours to about 5 hours. In the meantime, the present preparation is designed to gradually release the medicament therein after the above-mentioned predetermined lag time upon reaching the small intestine, and the chitosan part of the coating film is specifically decomposed due to its decomposition property specific to *Eschericia coli* upon reaching the large intestine, and then the medicament therein is released therefrom at an accelerated rate. In addition, another feature of the present solid preparation is to freely control the release of the medicament therefrom upon reaching the large intestine by changing the types and the grade of the water-insoluble polymer, the mixing ratio of the chitosan powder, and the grade and the particle diameter thereof, etc. According to the types of the medicament used therein, there may be a possibility of onset of undesirable side effects caused by the excess release of the medicament in the large intestine, but it is of advantage that the solid preparation of the present invention can be freely designed and controlled taking into consideration these points.

The Medicament is Released in the Large Intestine without Lag Time.

Chitosan usually needs a prescribed lag time for decomposition after it reaches the large intestine, but when the colonic delivery solid preparation of the present invention is used, the medicament therein is released through the water-insoluble coating film which becomes medicament-permeable after a prescribed period after passing through the stomach, therefore, it is advantage of the present preparation that the medicament is released without a lag time upon reaching the large intestine.

The Delivery of the Medicament into the Large Intestine is Controlled in Terms of Time and Site-Specificity.

A characteristic of the water-insoluble coating film having a chitosan powder dispersed therein (hereinafter, occasionally referred to as "chitosan powder-dispersing type coating film") is to enable the control of the delivery of the medicament into the large intestine in terms of time and site-specificity making use of the property of chitosan. Hitherto, only one of the time-control and the colon-specificity has been widely tried, but those attempts lacked the certainty of the release of the medicament in the large intestine. As compared with such conventional preparations, the solid preparation of the present invention enables controlling the release of the medicament and the release rate thereof either in the ascending colon, in the transverse colon, or in the descending colon, by changing the grades and the combination ratio of the water-insoluble polymer and chitosan, the grades and the particle diameters of chitosan, and the thickness of the films. In addition, by properly selecting a water-insoluble polymer and an enteric polymer, the present preparation enables the release of a medicament not only in the large intestine but also in the small intestine.

As shown in FIG. 11B, another embodiment of the present invention is a sustained release solid preparation containing chitosan powder, which is obtained by coating a medicament-containing solid material only with a water-insoluble coating film containing a chitosan and a water-insoluble polymer but not with an enteric coating film.

The process for producing the sustained release solid preparation containing chitosan powder is the same as that for the above-mentioned colonic delivery solid preparation except for the formation of the enteric coating film. That is, a coating solution for water-insoluble coating film having a chitosan powder dispersed therein is applied to a medicament-containing solid material such as a capsule, a tablet, or a pellet containing a medicament.

The sustained release solid preparation containing chitosan powder of the present invention is useful not only as a starting material for the above-mentioned colonic delivery solid preparation containing chitosan powder, but also it possesses the following pharmaceutical usefulness.

The Release of the Medicament in the Stomach

As mentioned above, since chitosan has a property of easily dissolving in a weak acidic solution, it can dissolve in an acidic solution, i.e., in the stomach, and hence, in the present solid preparation having no enteric coating film, a part of the chitosan dispersed in the water-insoluble coating film having a chitosan dispersed therein dissolves in the stomach whereby a part of the medicament contained therein is released in the stomach. On the other hand, in a conventional sustained release preparation obtained by coating with only a conventional water-insoluble coating film, a lag time for the release of the medicament may be often set up in order to achieve the sustained release property for a long time by coating only with a coating film. Since chitosan dissolves in the stomach in the case of sustained release solid preparation containing chitosan powder of the present invention, the above problems of the conventional preparations coated only with a conventional water-insoluble coating film can be overcome.

The Release of the Medicament in the Small Intestine

On the other hand, since the pH value of the small intestine is neutral, the chitosan in the sustained release solid preparation containing chitosan powder of the present invention does not usually dissolve out in the small intestine, and hence, the medicament therein continues to be released in the small intestine at a similar rate as that of the release of the medicament in the stomach.

The Release of the Medicament in the Large Intestine

Then, when the sustained release solid preparation containing chitosan powder of the present invention reaches the large intestine, the remaining chitosan which does not dissolve out in the stomach is decomposed by the bacteria being present in the large intestine, whereby the membrane of the surface of the preparation becomes more porous, i.e., the number of pores on the membrane of the surface increases, then the release rate of the medicament is accelerated. In general, since fluids are less in the large intestine than in the small intestine etc., the release of the medicament in the large intestine from a sustained release preparation coated with a conventional water-insoluble coating film is delayed and a sufficient release thereof cannot be achieved, but the release of the medicament from the present solid preparation in the large intestine wherein fluids are less is accelerated due to the specific property of chitosan, and hence, the problems of the preparation coated only with a conventional water-insoluble coating film can be overcome.

The characteristic of the chitosan powder-dispersing type coating film in a sustained release solid preparation is to enable the controlling the release of the medicament in the stomach, the small intestine and the large intestine in terms of both time and site-specificity making use of the property of chitosan. Hitherto, the control of time in a sustained release preparation has been widely tried, but those attempts lacked the certainty of the release of a medicament in the large intestine. As compared with such conventional preparations, the sustained release solid preparation of the present invention enables controlling the release of the medicament and the release rate thereof not only in the stomach and the small intestine but also in the ascending colon, in the transverse colon, or in the descending colon, by changing the grades and the combination ratios of the water-insoluble polymer and chitosan, the grades and the particle diameters of chitosan, and the thickness of the films.

Hereinafter, the colonic delivery solid preparation and the sustained release solid preparation having no enteric coating film of the present invention are illustrated in more detail by Examples, but the present invention should not be construed to be limited thereto.

Example 1

Production of Colonic Delivery Pellet Preparation

Nonpareil® 103 (purified sucrose spheres; 16/24 mesh; manufacture by Freund Industrial Co., Ltd.; 1450 g) is subjected to powder coating with acetaminophen (45 g) using as a binding solution an aqueous solution of hydroxypropyl methylcellulose 2910 (TC-5E (manufactured by Shin-Etsu Chemical Co., Ltd.)) to give medicament-containing cores. The medicament-containing cores (360 g) thus obtained are coated with a 5 w/w % solution of ethyl cellulose in ethanol (1500 g) wherein chitosan (FLONAC® C-100M (manufactured by Kyowa Tecnos Co., Ltd.); deacetylation degree: 91.6%; particle size: 80% passing through 100 mesh (=150 μm); 30 g) is dispersed to give a chitosan-dispersing ethyl cellulose-coated preparation. The preparation thus obtained is further coated with a coating solution (5 w/w %; 3000 g) wherein an enteric substance HPMCAS (manufactured by Shin-Etsu Chemical Co., Ltd.) is dissolved in a mixed solvent of ethanol and water (8:2) to give a pellet type solid preparation.

Example 2

Production of Colonic Delivery Capsule Preparation

A 2 hard gelatin capsule (about 65 mg per each) is filled with acetaminophen 30-fold trituration (200 mg) which is diluted with lactose, and the resulting capsule (about 265 mg per each, totally 250 g) is coated with a 4 w/w % solution of ethyl cellulose in ethanol (100 g) wherein chitosan (FLONAC® C-100M (manufactured by Kyowa Tecnos Co., Ltd.); 8 g) is dispersed to give a chitosan-dispersing ethyl cellulose-coated preparation. The preparation thus obtained is further coated with a coating solution (5 w/w %; 1000 g) wherein an enteric substance HPMCAS (manufactured by Shin-Etsu Chemical Co., Ltd.) is dissolved in a mixed solvent of ethanol and water (8:2) to give a capsule preparation.

Examples 3a-3c

Production of Capsule Preparation Coated with Chitosan-Dispersing Ethyl Cellulose A 2 hard gelatin capsule (about 65 mg per each) is filled with acetaminophen 30-fold trituration (200 mg) which is diluted with lactose, and the resulting capsules (about 265 mg per each, totally 250 g) are coated with a 4 w/w % solution of ethyl cellulose in ethanol wherein chitosan (FLONAC® C-100M (manufactured by Kyowa Tecnos Co., Ltd.)) is dispersed in an amount of (a) 8 g, (b) 4 g, (c) 2 g (i.e., ethyl cellulose:chitosan=4:8, 4:4, 4:2, respectively) to give three types (3a, 3b, 3c) of chitosan-dispersing ethyl cellulose-coated capsule preparations.

Examples 4a, 4b

Production of Capsule Preparation Coated with Chitosan-Dispersing Eudragit® RS A 2 hard gelatin capsule (about 65 mg per each) is filled with acetaminophen 30-fold trituration (200 mg) which is diluted with lactose, and the resulting capsules (about 265 mg per each, totally 250 g) are coated with a 4 w/w % solution of Eudragit® RS in ethanol wherein chitosan (FLONAC® C-100M (manufactured by Kyowa Tecnos Co., Ltd.)) is dispersed (a) in an amount of 8 g (Eudragit® RS:chitosan=4:8), or (b) in an amount twice thereof (Eudragit® RS:chitosan=8:16) to give two types (4a, 4b, respectively) of chitosan-dispersing Eudragit® RS-coated capsule preparations.

Examples 5a, 5b

Production of Capsule Preparation Coated with Chitosan-Dispersing Eudragit® RS A 2 hard gelatin capsule (about 65 mg per each) is filled with acetaminophen 30-fold trituration (200 mg) which is diluted with lactose, and the resulting capsules (about 265 mg per each, totally 250 g) are coated with (a) a 4 w/w % solution of Eudragit® RS in ethanol wherein chitosan (FLONAC® C-100M (manufactured by Kyowa Tecnos Co., Ltd.); 16 g) is dispersed (Eudragit®b RS:chitosan=8:16), or (b) a 4 w/w % solution of Eudragit® RS in ethanol wherein chitosan (FLONAC® C-60M (manufactured by Kyowa Tecnos Co., Ltd.); deacetylation degree: 89.9%; particle size: 99.6% passing through 60 mesh (=250 µm); 16 g) is dispersed (Eudragit® RS:chitosan=8:16) to give two types (5a, 5b, respectively) of chitosan-dispersing Eudragit® RS-coated capsule preparations.

Example 6

Production of Sustained Release Pellet Preparation Coated with Chitosan-Dispersing Eudragit® RS Nonpareil® 103 (16/24 mesh, mean particle diameter: 0.83 mm; manufactured by Freund Industrial Co., Ltd.; 1450 g) is subjected to powder coating with acetaminophen (900 g) using as a binding solution an aqueous TC-5E solution to give medicament-containing cores (mean particle diameter: 0.99 mm). The resulting medicament-containing cores (360 g) are coated with a 4 w/w % solution of Eudragit® RS in ethanol (2100 g) wherein chitosan (FLONAC® C-100M (manufactured by Kyowa Tecnos Co., Ltd.); 168 g) is dispersed to give a chitosan-dispersing Eudragit® RS-coated preparation (mean particle diameter: 1.3 mm).

Example 7

Production of Colonic Delivery Pellet Preparation

The chitosan-dispersing Eudragit® RS-coated preparation obtained in Example 6 is coated with a coating solution which is obtained by dissolving an enteric substance Eudragit® L100-55 in ethanol (1500 g) at a concentration of 5 w/w %, and further dispersing magnesium stearate (80 g) therein to give a pellet solid preparation (mean particle diameter: 1.4 mm).

Dissolution Test

The preparations obtained in Examples 1 to 5b were subjected to the dissolution test by Paddle method using Japanese Pharmacopoeia 1st Fluid (pH 1.2, hereinafter, simply referred to as 1st Fluid) and/or Japanese Pharmacopoeia 2nd Fluid (pH 6.8, hereinafter, simply referred to as 2nd Fluid) as defined in the Thirteenth Edition of the Pharmacopoeia of Japan, and the dissolution pattern of the medicament released therefrom was observed (test solution for dissolution: 900 ml, 37° C., paddle rotation speed: 100 rpm). The results thereof are shown in FIG. 1 to FIG. 6, respectively.

Figure 7:
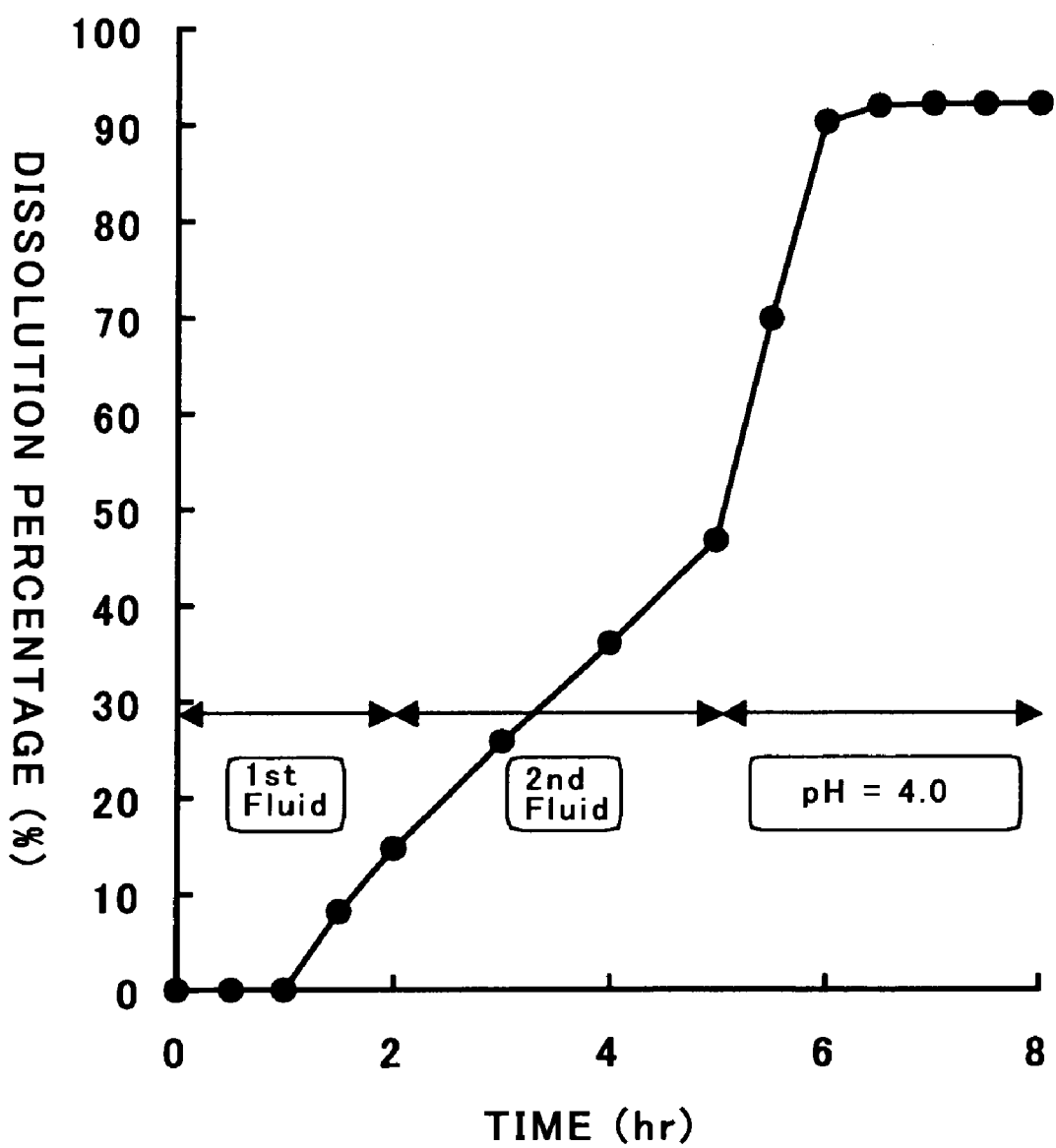
FIG. 7 shows the relation between the dissolution percentage of the medicament and the time of the sustained release pellet preparation of Example 6 in a similar dissolution test using Japanese Pharmacopoeia 1st Fluid, Japanese Pharmacopoeia 2nd Fluid and the solution of pH 4.0.
Figure 9:
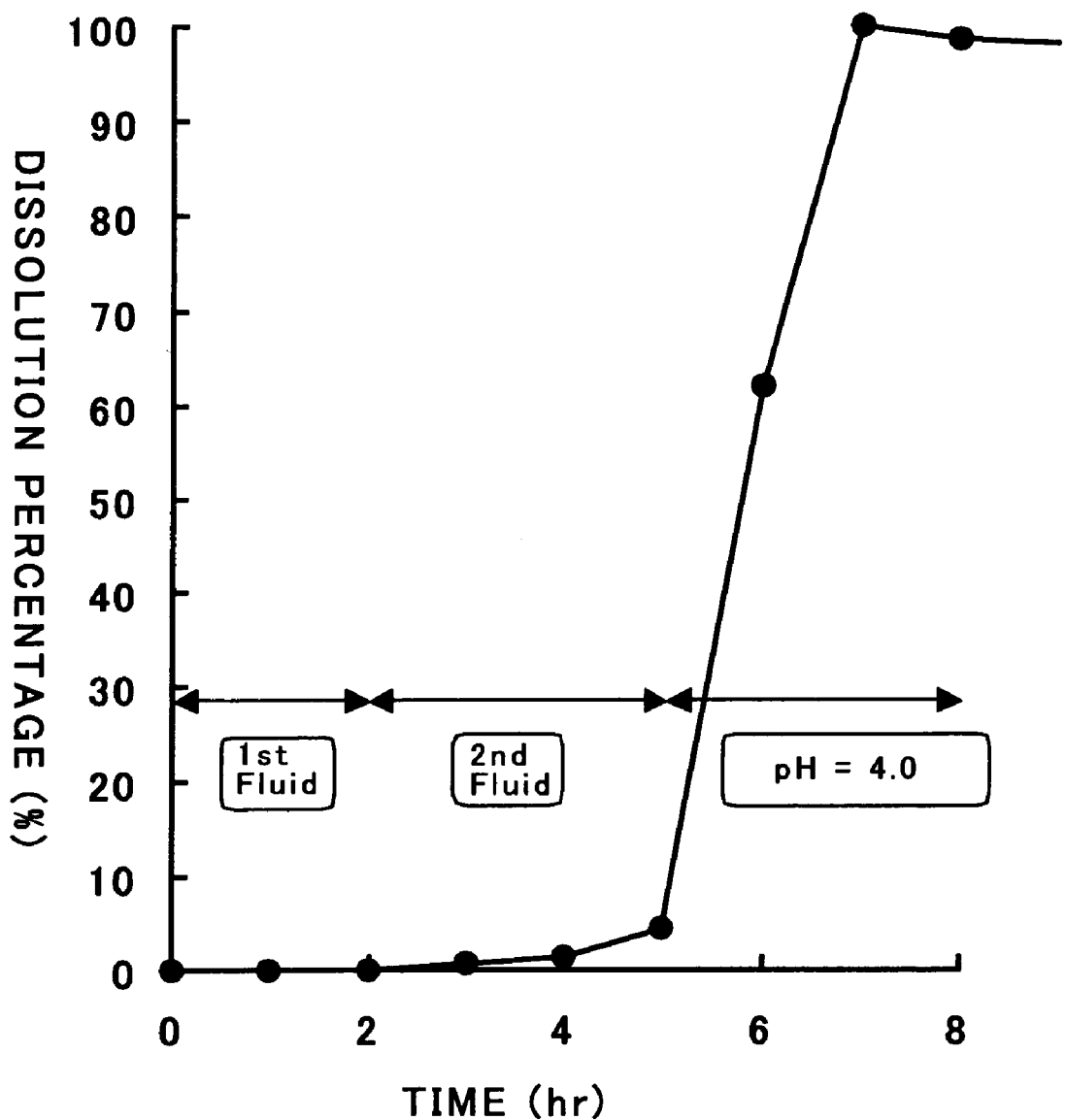
FIG. 9 shows the relation between the dissolution percentage of the medicament and the time of the colonic delivery pellet preparation of Example 7 in a similar dissolution test using Japanese Pharmacopoeia 1st Fluid, Japanese Pharmacopoeia 2nd Fluid and the solution of pH 4.0.

The preparations obtained in Example 6 and Example 7 were subjected to the dissolution test successively in 1st Fluid for 2 hours, then in 2nd Fluid for 3 hours, and then in a solution of pH 4.0, and the dissolution pattern of the medicament released therefrom was observed (test solution for dissolution: 900 ml; 37° C.; basket rotation speed: 100 rpm). The results thereof are shown in FIG. 7 and FIG. 9, respectively.

In the dissolution test, a preparation from which the medicament does not substantially dissolve out in more than 2 hours in 1st Fluid, a simulate model for gastric juice, and substantially dissolves out in a period of 2 to 5 hours in 2nd Fluid, a simulate model for intestinal fluid, and then a good dissolution of the medicament is achieved thereafter, i.e., a preparation from which the medicament does not dissolve out for more than 2 hours in the stomach, but after reaching the intestine, the medicament starts to dissolve out in 2-5 hours and almost of the medicament dissolves out in a designated period, is regarded as a preparation satisfying the object of the present invention.

Measurement of Blood Concentration In Vivo

Figure 8:
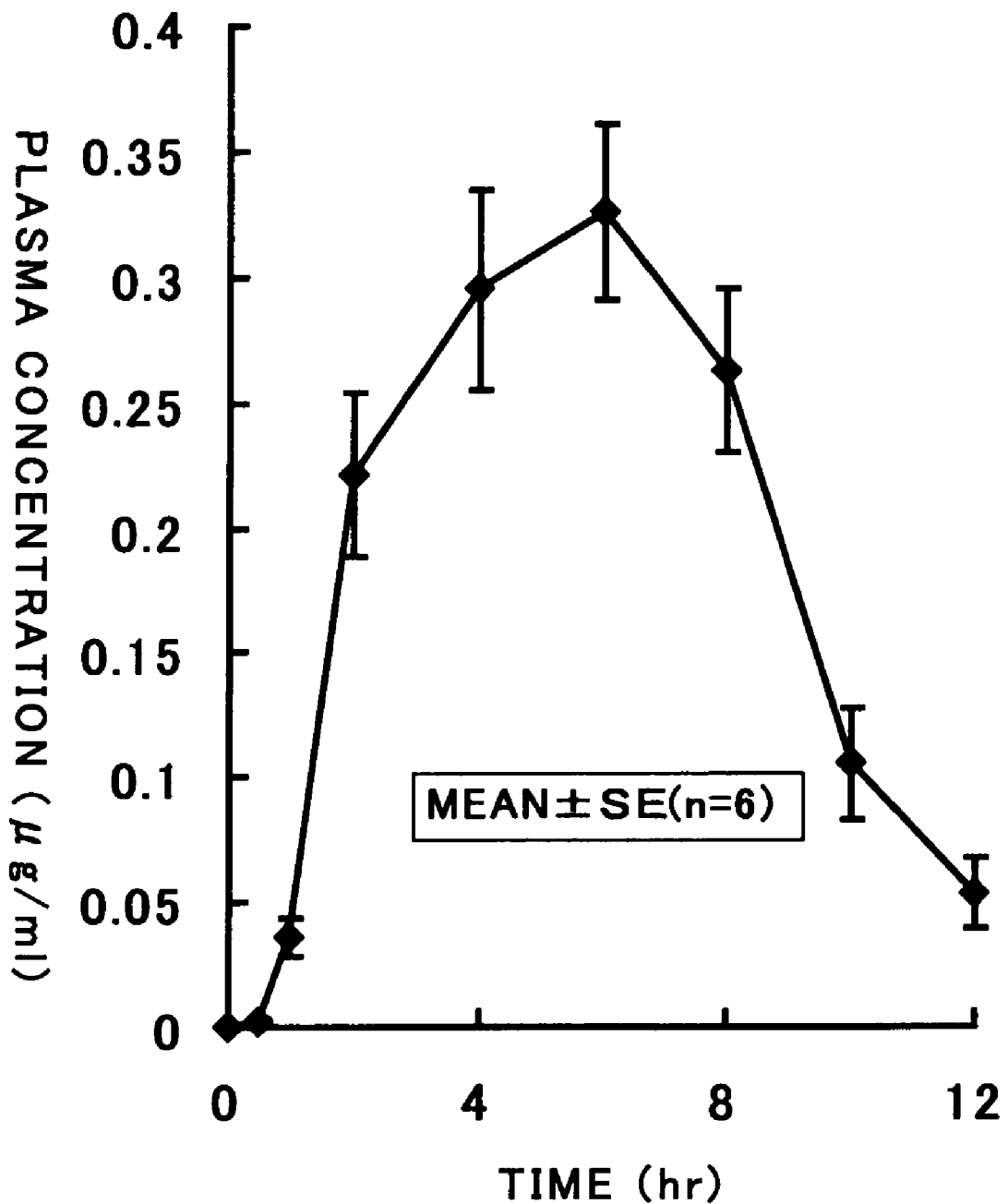
FIG. 8 shows the plasma concentration time curve of the medicament when the sustained release pellet preparation of Example 6 was administered to rats.
Figure 10:
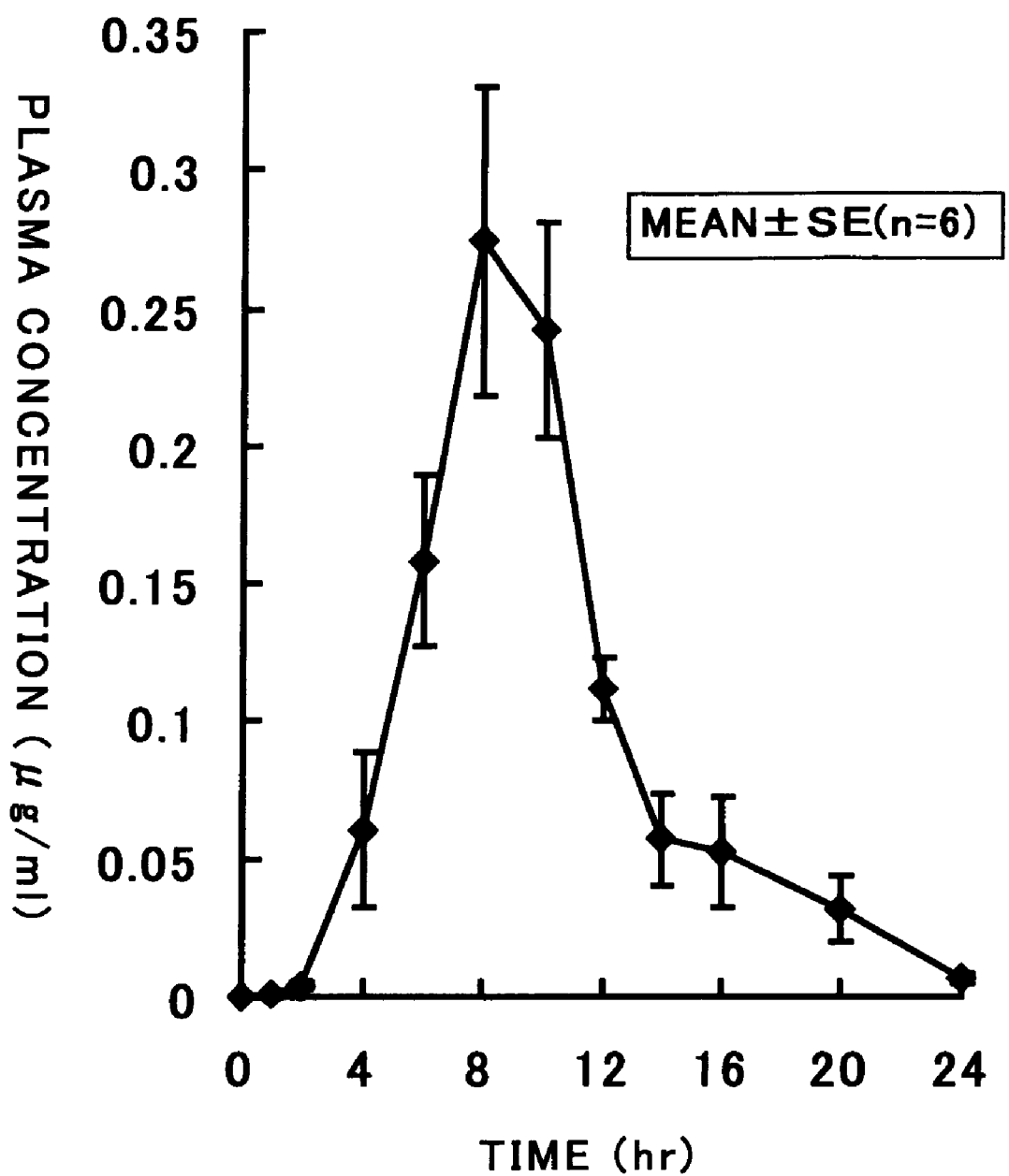
FIG. 10 shows the plasma concentration time curve of the medicament, when the colonic delivery pellet preparation of Example 7 was administered to rats.

To Wistar male rats (weighing about 200 g, 6 animals) was administered the pellet preparation obtained in Example 6 or Example 7 (9 mg or 12 mg, respectively, equivalent of 2 mg of acetaminophen), and the blood samples were collected at designated time intervals, and the acetaminophen concentration in the plasma was measured. The results thereof are shown in FIG. 8 and FIG. 10, respectively.

Figure 2:
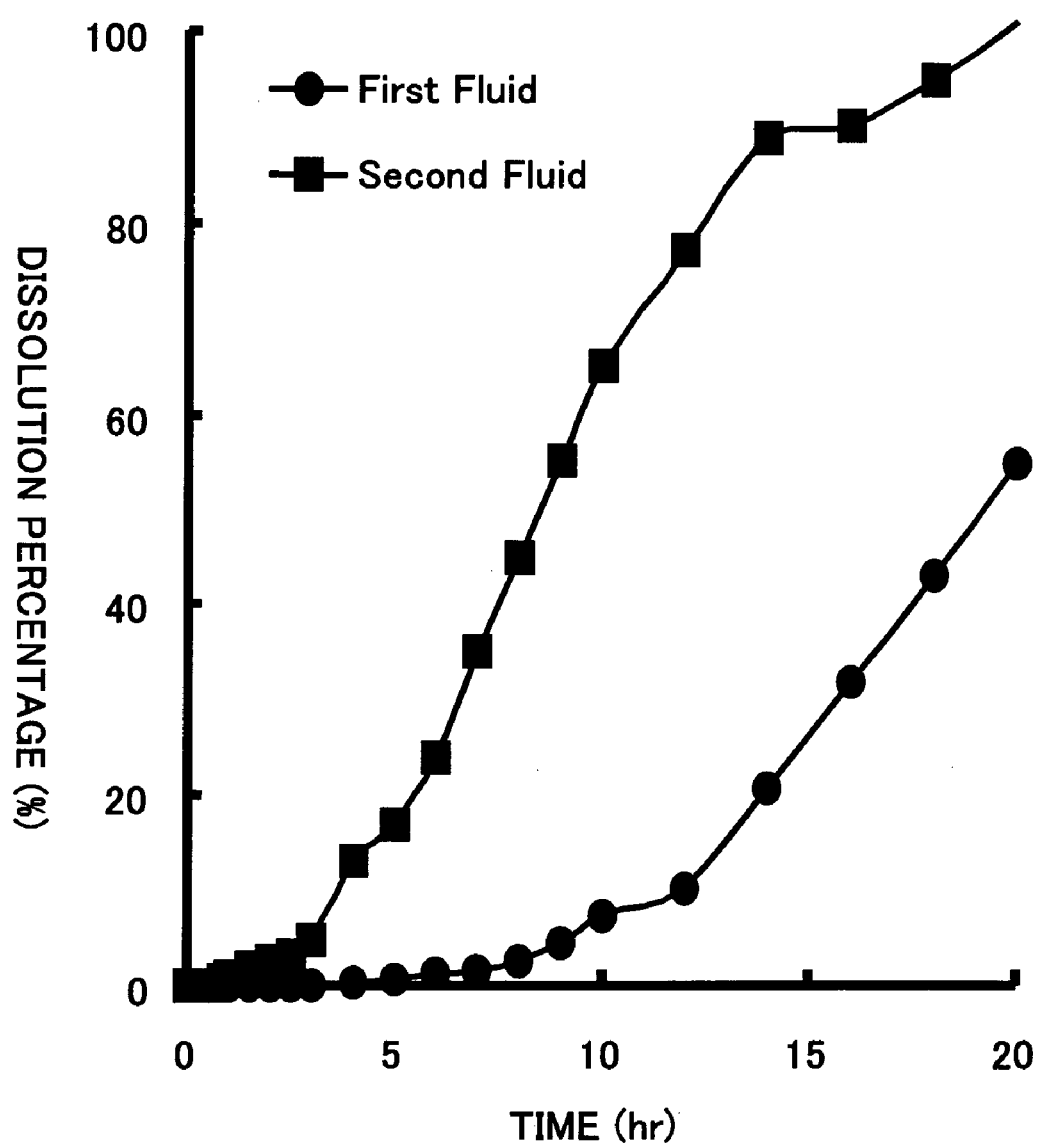
FIG. 2 shows the relation between the dissolution percentage of the medicament and the time of the colonic delivery capsule preparation of Example 2 in a similar dissolution test using Japanese Pharmacopoeia 1st Fluid and Japanese Pharmacopoeia 2nd Fluid.

As shown in FIG. 1, the preparation of Example 1 hardly released the medicament therefrom in 1st Fluid even 4 hours after the start of the dissolution test. In 2nd Fluid, the preparation of Example 1 had a lag time of 4 hours, and then started to gradually release the medicament 4 hours after the start of the dissolution test, and then at 20 hours after the start of the dissolution test, about 100% of the medicament dissolved out. Therefore, the preparation of Example 1 is a good preparation satisfying the above criteria. As shown in FIG. 2, the preparation of Example 2 hardly release the medicament in 1st Fluid even 2 hours after the start of the dissolution test, and had a lag time of 3 hours until the medicament started to dissolve out in 2nd Fluid, and then started to gradually release the medicament 3 hours after the start of the dissolution test, and about 95% of the medicament dissolved out 18 hours after the start of the dissolution test. Therefore, the preparation of Example 2 is a good preparation for satisfying the above criteria.

In the experiments as shown in FIG. 3 to FIG. 6 as mentioned below, preparations having no enteric coating film were used in 2nd Fluid in which the pH value was proximate to that in the intestine (including the large intestine), in order to observe the behavior thereof only in the intestine.

Figure 3:
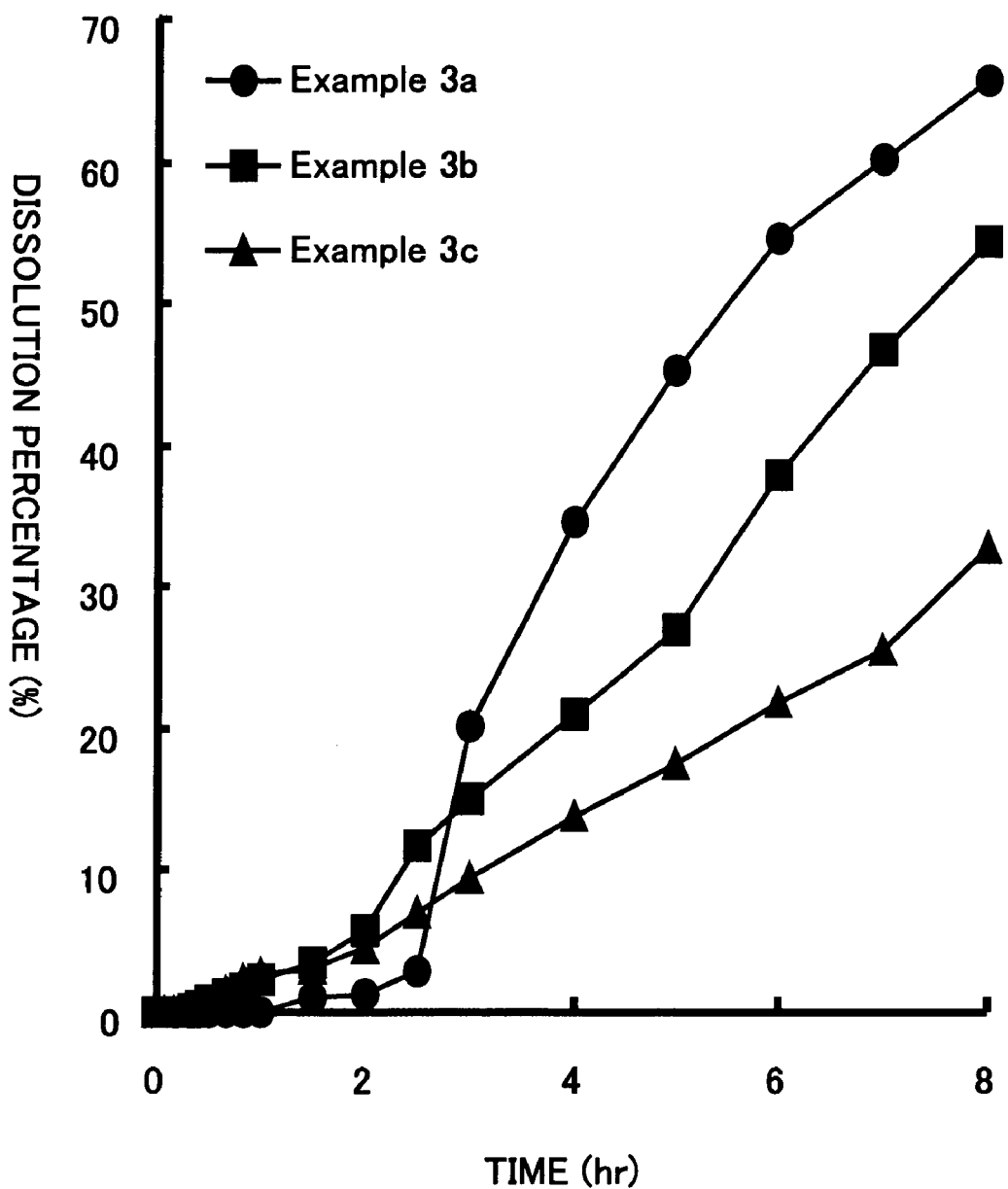
FIG. 3 shows the relation between the dissolution percentage of the medicament and the time in a similar dissolution test using Japanese Pharmacopoeia 2nd Fluid when applied to the capsule preparations of Examples 3a to 3c, wherein the addition ratio of the chitosan powder in the water-insoluble polymer coating film having a chitosan powder dispersed therein was changed as 1 fold, ½ fold and ¼ fold, respectively.

As shown in FIG. 3, the preparations of Example 3b and Example 3a, in which the amount of chitosan was doubled or quadrupled to that in the preparation of Example 3c, respectively, showed an increase in the dissolution percentage of the medicament in 2nd Fluid in a constant ratio to the increase of the chitosan amount. That is, by determining the amount of chitosan in this manner, the dissolution percentage of the medicament can be controlled within a range of about 30% to about 65% 8 hours after the start of the dissolution test.

Therefore, it is suggested from FIG. 3 that in the enteric coated preparation of the present invention, the dissolution percentage of the medicament therefrom in the large intestine can be controlled by changing the amount of chitosan contained therein.

Figure 4:
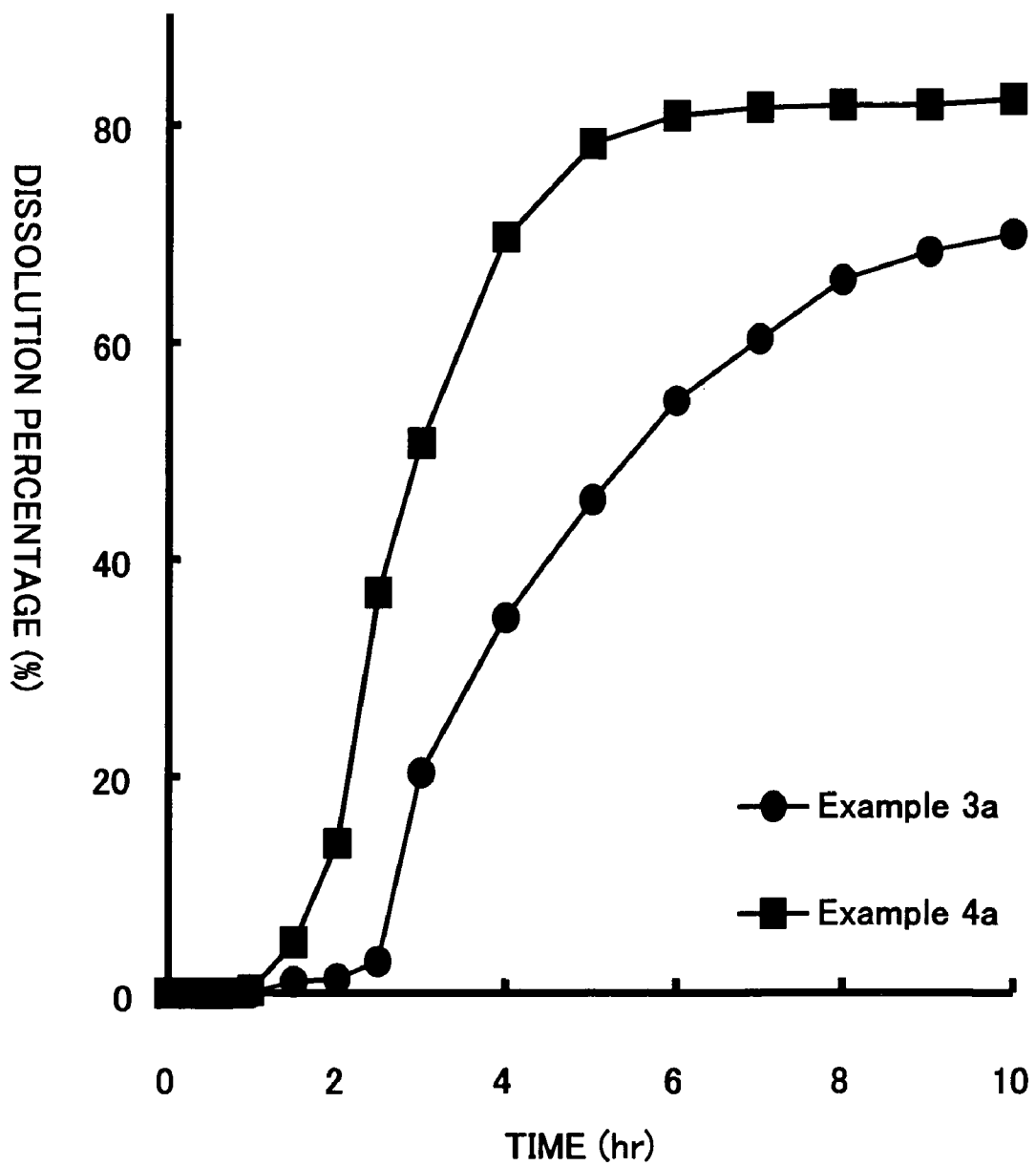
FIG. 4 shows the relation between the dissolution percentage of the medicament and the time in a similar dissolution test using Japanese Pharmacopoeia 2nd Fluid when applied to the capsule preparations using different kinds of a water-insoluble substance of Example 3a (the water-insoluble substance: ethyl cellulose) and Example 4a (the water-insoluble substance: Eudragit® RS).

As shown in FIG. 4, in the preparation of Example 3a obtained by using ethyl cellulose as a water-insoluble polymer, the medicament started to dissolve out therefrom about 2 hours after the start of the dissolution test, and the dissolution percentage of the medicament measured up to about 70% 10 hours after the start of the dissolution test. On the other hand, in the preparation of Example 4a obtained by using Eudragit® RS as a water-insoluble polymer, the medicament started to dissolve out therefrom about 1 hour and half after the start of the dissolution test, and the dissolution percentage of the medicament already reached about 80% 5 hours after the start of the dissolution test.

Therefore, it is suggested from FIG. 4 that in the enteric coated preparation of the present invention, the dissolution percentage of the medicament therefrom in the large intestine can be controlled by changing the types of the water-insoluble polymer.

Figure 5:
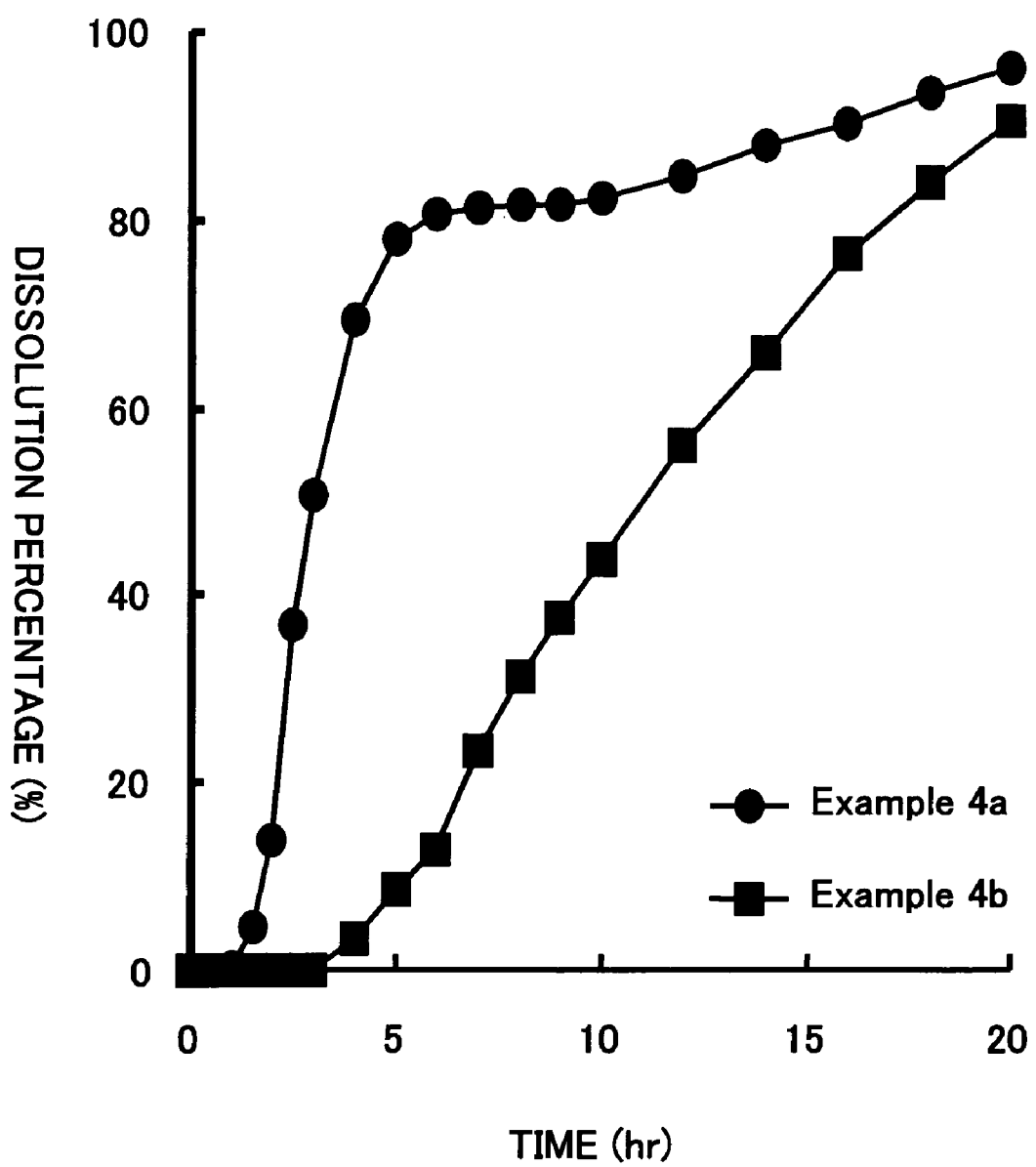
FIG. 5 shows the relation between the dissolution percentage of the medicament and the time in a similar dissolution test using Japanese Pharmacopoeia 2nd Fluid when applied to the capsule preparations of Example 4a and Example 4b, wherein the coating amount of the water-insoluble coating film having a chitosan powder dispersed therein was changed.

As shown in FIG. 5, in the preparation of Example 4a, the medicament started to dissolve out about 2 hours after the start of the dissolution test, and the dissolution percentage thereof reached about 80% about 5 hours after the start of the dissolution test. On the other hand, in the preparation of Example 4b wherein the amount of the water-insoluble coating film was doubled to that of the preparation of Example 4a, the medicament started to dissolve out in 2nd Fluid about 4 hours after the start of the dissolution test, and thereafter, the dissolution percentage was gradually increased and reached about 90% 20 hours after the start of the dissolution test.

Therefore, it is suggested from FIG. 5 that in the enteric coated preparation of the present invention, the dissolution percentage of the medicament therefrom in the large intestine can be controlled by changing the thickness of the chitosan powder-dispersing water-insoluble coating film.

Figure 6:
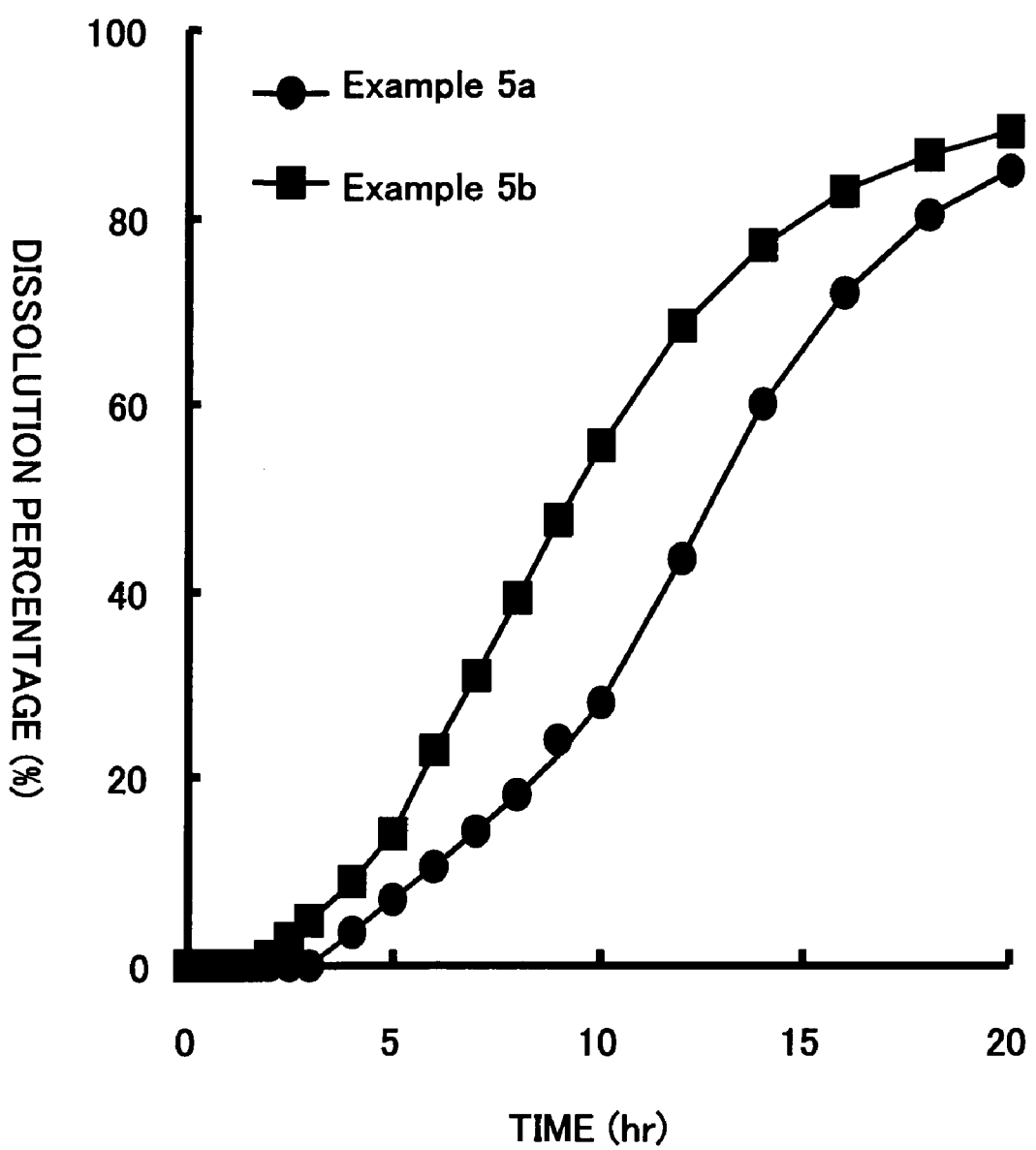
FIG. 6 shows the relation between the dissolution percentage of the medicament and the time in a similar dissolution test using Japanese Pharmacopoeia 2nd Fluid when applied to the capsule preparations of Example 5a and Example 5b, wherein the chitosan powders dispersed in the water-insoluble coating film had a different particle diameter of 100 mesh (100 M) or 60 mesh (60 M), respectively.

As shown in FIG. 6, in the preparation of Example 5b wherein the chitosan having a particle diameter of 60 mesh (particle size: 99.6% passing through 60 mesh (=250 μm)) was used, the medicament started to dissolve out about 2 hours and half after the start of the dissolution test, and the dissolution percentage thereof reached about 55% about 10 hours after the start of the dissolution test, and thereafter, the medicament gradually continued to dissolve out, and the dissolution percentage thereof reached about 90% 20 hours after the start of the dissolution test. On the other hand, in the preparation of Example 5a wherein the chitosan having a particle diameter of smaller than 60 mesh (particle diameter: 100 mesh; particle size: 80% passing through 100 mesh (=150 μm)) was used, the medicament started to dissolve out in 2nd Fluid about 4 hours after the start of the dissolution test, and the dissolution percentage thereof reached about 30% 10 hours after the start of the dissolution test, and thereafter, the medicament continued to dissolve out, and the dissolution percentage thereof reached about 85% 20 hours after the start of the dissolution test.

Therefore, it is suggested from FIG. 6 that in the enteric coated preparation of the present invention, the dissolution percentage of the medicament therefrom in the large intestine can be controlled by changing the particle diameter of chitosan to be dispersed.

As is apparent from the above explanation of FIG. 3 to FIG. 6, the dissolution pattern of the medicament can be controlled by changing the ratio of a water-insoluble substance to a chitosan powder, the types and the amount of the water-insoluble coating film, and the particle diameter of chitosan, so that a desired colonic delivery solid preparation can be designed.

FIG. 7 and FIG. 8 concern the dissolution of the medicament in the sustained release preparation. As shown in FIG. 7, in the preparation of Example 6, which is a preparation having no enteric coating film, the medicament started to dissolve out therefrom in 1st Fluid, and further the medicament continuously dissolved out at a constant rate in 2nd fluid, which replaced 1st Fluid, and then rapidly dissolved out in a weak acidic solution, which replaced 2nd Fluid.

As shown in FIG. 8, there was obtained the profile of the plasma concentration of the medicament in the animal test (in vivo), which showed the effects of the chitosan being dispersed in the water-insoluble polymer on the release of the medicament in the stomach and in the large intestine, and it was indicated that the release of the medicament lasted for 12 hours.

As shown in FIG. 9, in the preparation of Example 7, the medicament hardly dissolved out in 1st Fluid 2 hours after the start of the dissolution test, and after replacing 1st Fluid by 2nd Fluid, the preparation of Example 7 showed a lag time of about 3 hours for dissolution, and then almost 100% of the medicament rapidly dissolved out under weak acidic conditions. Therefore, the preparation of Example 7 is a good preparation satisfying the above criteria.

As shown in FIG. 10, it was indicated that the plasma concentration of medicament in the animal test (in vivo) reached the maximum 8 hours after the administration of the pellet preparation, and the preparation showed the colonic specific release of the medicament as well as the sustained release of the medicament.

INDUSTRIAL APPLICABILITY

Since the colonic delivery solid preparation containing chitosan powder of the present invention can be produced without using an acid as a solvent, there is no influence of the acid to remain, and the transit of the medicament into the large intestine can be controlled both time-dependently and site-specifically by a chitosan dispersing type coating film making use of the property of chitosan so that the present colonic delivery solid preparation is an excellent colonic delivery solid preparation containing chitosan powder. In addition, a process for producing the colonic delivery solid preparation containing chitosan powder of the present invention is an excellent and simple process being suitable for large-scale production. Further, the solid preparation having no enteric coating film is useful not only as a solid preparation for producing the colonic delivery solid preparation containing chitosan powder of the present invention, but also it in itself shows a sustained release property and also is useful as a sustained release preparation making use of the properties of chitosan.

The invention claimed is:

1. A sustained release preparation comprising a medicament-containing solid material and a water-insoluble coating film, wherein said medicament-containing solid material consists of a medicament and a pharmaceutical excipient, and said water-insoluble coating film consists essentially of a water-insoluble polymer and a chitosan powder dispersed in said polymer, wherein said polymer is selected from the group consisting of ethyl cellulose, ethyl acrylate-methyl methacrylate-trimethylammoniumethyl methacrylate chloride copolymer, and methyl methacrylate-ethyl acrylate copolymer, said chitosan powder having a mean particle size diameter in the range of about 0.5 µm to about 400 µm, and the weight ratio of said polymer and said chitosan powder is from 4:1 to 1:4.

2. The sustained release preparation of claim 1, which further comprises a coating with an enteric polymer, wherein said enteric polymer is selected from the group consisting of hydroxypropyl methylcellulose acetate succinate, hydroxypropyl methylcellulose phthalate, and methacrylic acid-ethyl acrylate copolymer.

3. The sustained release preparation according to claim 1, wherein the medicament-containing solid material is selected from the group consisting of a pellet, a capsule, and a tablet.

4. The sustained-release preparation according to claim 2, wherein the medicament-containing solid material is selected from the group consisting of a pellet, a capsule, and a tablet.

5. A process for producing the sustained release preparation of claim 1, which comprises the steps of
   (1) coating a medicament-containing solid material with a coating solution obtained by dispersing a chitosan powder in a solution of a water-insoluble polymer in ethanol or water to form a water-insoluble coating film onto the medicament-containing solid material, wherein said polymer is selected from the group consisting of ethyl cellulose, ethyl acrylate-methyl methacrylate-trimethylammoniumethyl methacrylate chloride copolymer, and methyl methacrylate-ethyl acrylate copolymer, said chitosan powder having a mean particle size diameter in the range of about 0.5 µm to about 400 µm, and the weight ratio of said chitosan powder to said water-insoluble polymer is in the range of about 1:4 to about 4:1, and
   (2) removing the ethanol or water by drying the coated preparation.

6. The process for producing the sustained release preparation according to claim 5, which further comprises a step of coating the preparation of claim 5 with an enteric polymer, wherein the enteric polymer is selected from the group consisting of hydroxypropyl methylcellulose acetate succinate, hydroxypropyl methylcellulose phthalate and methacrylic acid-ethyl acrylate copolymer.

* * * * *

UNITED STATES PATENT AND TRADEMARK OFFICE
CERTIFICATE OF CORRECTION

PATENT NO. : 7,604,820 B1 Page 1 of 1
APPLICATION NO. : 10/048063
DATED : October 20, 2009
INVENTOR(S) : Shimono et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 215 days.

Signed and Sealed this

Fifth Day of October, 2010

David J. Kappos
*Director of the United States Patent and Trademark Office*